(12) United States Patent  
Wiesendanger et al.

(10) Patent No.: US 7,087,696 B2  
(45) Date of Patent: Aug. 8, 2006

(54) UV-CURABLE EPOXY ACRYLATES

(75) Inventors: Rolf Wiesendanger, Riehen (CH); Michael Reisinger, Himmelried (CH)

(73) Assignee: Huntsman Advanced Materials Americas Inc., The Woodlands, TX (US)

( * ) Notice: Subject to any disclaimer, the term of this patent is extended or adjusted under 35 U.S.C. 154(b) by 0 days.

(21) Appl. No.: 10/537,656

(22) PCT Filed: Dec. 18, 2003

(86) PCT No.: PCT/EP03/51057

§ 371 (c)(1),
(2), (4) Date: Jun. 6, 2005

(87) PCT Pub. No.: WO2004/056930

PCT Pub. Date: Jul. 8, 2004

(65) Prior Publication Data

US 2006/0052628 A1   Mar. 9, 2006

(30) Foreign Application Priority Data

Dec. 19, 2002   (CH) ..................... 2161/02

(51) Int. Cl.
*C08F 20/20* (2006.01)
*C07C 69/52* (2006.01)
(52) U.S. Cl. ....................... 526/327; 560/220
(58) Field of Classification Search ............ None
See application file for complete search history.

(56) References Cited

U.S. PATENT DOCUMENTS 5,277,739 A * 1/1994 Muller et al. ............ 156/330.9

* cited by examiner

*Primary Examiner*—Paul A. Zucker
(74) *Attorney, Agent, or Firm*—Robert Holthus

(57) ABSTRACT

Epoxy acrylates of the formulae (A), (B) and epoxy acrylate mixtures comprising at least one of the compounds (A) or (B) are novel and find use in coating materials or adhesives featuring high UV stability

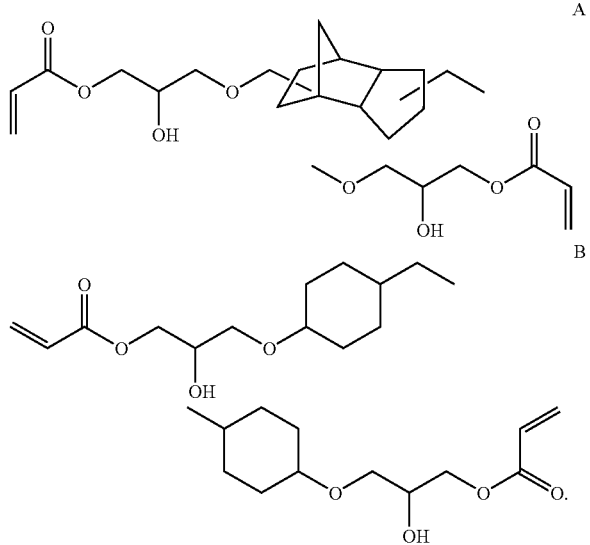

10 Claims, No Drawings

UV-CURABLE EPOXY ACRYLATES

CROSS REFERENCE TO RELATED APPLICATIONS

This application is the National Phase of International Application PCT/EP2003/051057 filed Dec. 18, 2003 which designated the U.S. and which claims priority to Swiss Pat. App. No. 2161/02 filed Dec. 19, 2002. The noted applications are incorporated herein by reference.

The present invention relates to novel epoxy acrylates and epoxy acrylate mixtures, to a process for the preparation and to the use of the epoxy acrylates of the Invention in coating materials or adhesives with high UV stability, and also to coating compositions and adhesive compositions.

Epoxy acrylates are compounds prepared by reacting epoxides, either glycidyl ethers or cyclohexene oxides, with acrylic acid, that is producing hydroxyacrylates.

By way of example the aromatic, industrially widespread BPA-DGE (e.g Araldit® GY240) or epoxyphenol novolaks (e.g. Araldit® EPN 1179) are reacted to the corresponding hydroxyacrylates. These are available commercially (from BASF, Cray Valley, UCB). Common to these products are viscosities of about 500–1000 Pas (25° C.) in the undiluted state. For reasons of handling and processing they are generally diluted with a low-viscosity (5–50 mPas, 25° C.) acrylic monomer, such as HDDA, TMPTA, TPGDA, and other monomers known to the person skilled in the art. Radiation-induced free-radical curing of such products produces films having good mechanical properties. Typical surface hardnesses (Persoz hardness) of such "neat resin" homopolymers are 300–330 seconds. However, these high hardnesses are accompanied by Erichsen indentation values of <1 mm. Use is made generally of aromatic epoxy acrylates when scratch resistance and chemical resistance are priorities. Aromatic compounds are unsuitable in films exposed to weathering. In artificial weathering in a Weather-O-meter, for example, severe loss of gloss and yellowing are observed within 100 hours.

Epoxy acrylates made from linear aliphatic alcohols are also known. Commercially available examples include butanediol diglycidyl diacrylate and hexanediol diglycidyl diacrylate. They are notable for a low viscosity (about 1 Pa*s, 25° C.) and solubility in water. Homopolymers, however, have weak mechanical properties. Neat resin Persoz hardnesses of around 50 seconds are commonplace.

The known epoxy acrylates, however, are not entirely satisfactory, particularly when not only outstanding mechanical properties but also high UV stabilities are required. In many cases the known epoxy acrylates also have a considerable odour.

It was an object of the present Invention, therefore, to find odourless epoxy acrylate compositions having both outstanding mechanical properties and high UV stabilities.

Surprisingly it has now been found that homopolymers of the novel compound of the formula

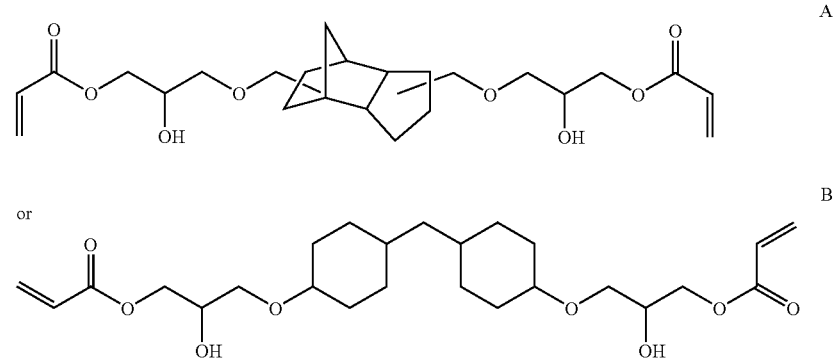

meet the specified objectives. Also advantageous in the sense of the object to be achieved is an epoxy acrylate mixture comprising A and B or an epoxy acrylate mixture which in addition to the compound of the formula A or B comprises at least one compound of the formula

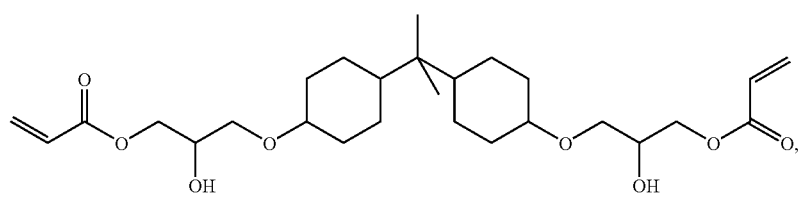

-continued

D

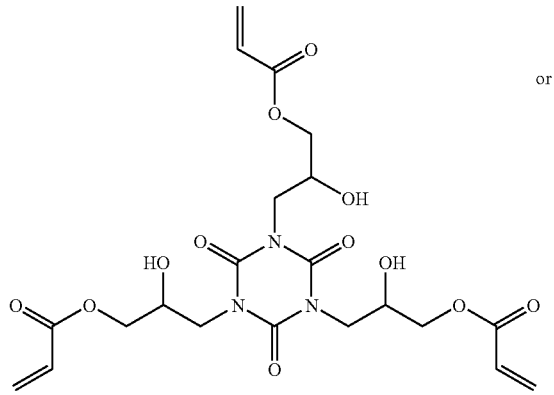

or

E

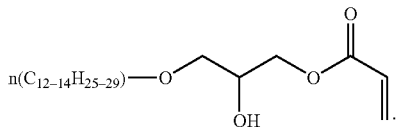

The addition of compound D can be used to increase the network density. By adding compound E it is possible to set a favourable (reduced) working viscosity. Preferably, the epoxy acrylate mixtures according to the invention contain as epoxy acrylates at least 30% by weight, more preferably, at least 50% by weight, of compound A and/or B.

In this way compositions are achieved which have a solids content of 100%, are odourless, and have good mechanical properties and high UV stabilities. The compositions of the invention display the stated advantages when irradiated even with a low UV dose and are also suitable, when using corresponding monomers containing acceptor groups (such as NCO or COOR, for example), for the process known as dual cure, where an additional thermal cure is accomplished.

The novel compounds A and B can be prepared in a conventional manner by reacting the corresponding diglycidyl ethers with acrylic acid, preferably in a near-equinormal ratio of from 1:0.9 to 1:1.1. Further details and preferences are evident from the examples. Also of advantage is the simultaneous reaction of different glycidyl ethers with acrylic acid, leading directly to a composition of the Invention comprising at least one compound A or B and also at least one further compound A to E.

The present invention provides for the use of the epoxy acrylates of the invention in coating compositions and adhesive compositions.

The present invention further provides a radiation-curable coating composition based on an epoxy acrylate binder containing from 5 to 90% by weight, preferably from 10 to 80% by weight, of the epoxy acrylate of the Invention, based on the total amount of binder.

The present invention further provides a radiation-curable adhesive composition based on an epoxy acrylate binder containing from 5 to 90% by weight, preferably from 10 to 80% by weight, of the epoxy acrylate of the invention, based on the total amount of binder.

The radiation-curable compositions of the Invention normally include a photoinitiator. The photoinitiator content is preferably from 0.1 to 10% by weight and in particular from 1 to 8% by weight, based in each case on the total amount of the epoxy acrylates. Suitable photoinitiators are known to the person skilled in the art and some are also available commercially. Use may be made, for example, of the products available commercially under the name Irgacure® from Ciba Spezialitätenchemie. In the case of optional hybrid system compositions comprising an oxirane compound, use is additionally made of initiators for photocationic polymerization, which are likewise known to the person skilled in the art. Photoinitiators for cationic polymerization generate strong Brönsted acids when exposed to UV radiation and thereby Initiate the polymerization of the epoxide groups. The compositions contain cationic photoinitiators generally in amounts from 0.05 to 3% by weight, based on the epoxy resin component. By way of example, cationic photoinitiators have as their general formula either $S^+(A_1A_2A_3)Q^-$ or $I^+(A_1A_2)Q^-$, in which $A_1$, $A_2$ and $A_3$ are identical or different aromatic radicals, which may be singly or multiply substituted and can contain heteroatoms, and $Q^-$ is an anion such as $BF_4^-$, $PF_6^-$, $AsF_6^-$, $SbF_6^-$ or $SnCl_6^-$, for example. Examples of commercial products of the formula $S^+(A_1A_2A_3)Q^-$ are UVI-6974 ($Q^-=SbF_6^-$, Union Carbide), SP 170 ($Q^-=SbF_6^-$, Asahi Denka Kogyo K.K.) or K 185 ($Q^-=PF_6^-$, Sartomer). Examples of commercial products of the formula $S^+(A_1A_2A_3)Q^-$ are CD 1012 ($Q^-=SbF_6^-$, Sartomer), UV 9380C ($Q^-=SbF_6^-$, General Silicon) or CGI-552 ($Q^-=PF_6^-$, Ciba SC). The foregoing list is not exhaustive.

Besides the photoinitiators, suitable sensitizers can be used in effective amounts.

The compositions of the invention are advantageously cured with actinic radiation, with UV radiation or with electron beams. Where appropriate this can be carried out with or supplemented by actinic radiation from other sources. In the case of electron beams it is preferred to operate under an Inert gas atmosphere. This can be ensured, for example, by supplying carbon dioxide and/or nitrogen directly to the surface of the coating. In the case of UV radiation curing as well it Is possible to operate under inert gas in order to prevent formation of ozone.

Curing with actinic radiation Is carried out using the conventional and known radiation sources and optical auxiliary measures. Examples of suitable radiation sources are high-pressure or low-pressure mercury vapour lamps, which are described for example in the brochures from Fusion Systems Inc. or Heraeus Holding GmbH. Their arrangement is known In principle and can be adapted to the circumstances of the workpiece and the process parameters. In the case of workpieces of complex shape those regions not accessible to direct radiation (shadow regions), such as cavities, folds and other structural undercuts, can be (partly) cured using pointwise, small-area or all-round sources in conjunction with an automatic movement means for the irradiation of cavities or edges.

During the curing of the film or films of the composition of the invention that is or are present thereon using actinic radiation, the substrate can be at rest or can be guided past the radiation source at an appropriate speed. The UV lamps here are preferably of 100 to 200 W/cm, more preferably from 120 to 190 W/cm and in particular from 140 to 180 W/cm. Irrespective of whether the substrate is moved or is at rest, a radiation dose in the range from 50 to 6,000 mJ/cm$^2$, more preferably from 50 to 2,000 mJ/cm$^2$, proves to be advantageous.

The compositions of the invention may further comprise the epoxy resins, preferably aliphatic epoxy resins, which are customary in epoxy resin technology. Examples of such epoxy resins Include the following:

I) Polyglycidyl ethers or poly-(β-methylglycidyl)ethers, obtainable by reacting a compound having at least one, preferably two, free alcoholic hydroxyl groups with epichlorohydrin or β-methylepichlorohydrin under alkaline conditions or in the presence of an acidic catalyst with subsequent alkali treatment.

The glycidyl ethers of this type are derived for example from acyclic alcohols, such as ethylene glycol, diethylene glycol or higher poly(oxyethylene)glycols, propane-1,2-diol or poly(oxypropylene)glycols, propane-1,3-diol, butane-1,4-diol, poly(oxytetramethylene)glycols, pentane-1,5-diol, hexane-1,6-diol, hexane-2,4,6-triol, glycerol, C$_{12\text{-}14}$OH (Araldit® DY-E) 1,1,1-trimethylolpropane, pentaerythritol, sorbitol, and also from polyepichlorohydrins. Other glycidyl ethers of this type are derived from cycloaliphatic alcohols, such as 1,4-cyclohexanedimethanol, bis(4-hydroxycyclohexyl)methane, 2,2-bis(4-hydroxycyclohexyl)-propane or tricyclodecanedimethanol.

II) Cycloaliphatic epoxy resins, such as bis(2,3-epoxycyclopentyl)ether, 2,3-epoxycyclopentylglycidyl ether, 1,2-bis (2,3-epoxycyclopentyloxy)ethane or the corresponding hydrogenated bisphenol A diglycidyl ethers, bisphenol F diglycidyl ethers, or TCD diglycidyl ethers.

Particularly preferred additional epoxy resins used are aliphatic epoxy resins such as trimethylolpropane triglycidyl ether and also cycloaliphatic epoxy resins such as bis(2,3-epoxycyclopentyl)ether.

Besides the components named, the compositions of the invention may of course comprise other components, which may differ according to the field of use of the compositions, and which are known to the person skilled in the particular art field.

Coating compositions based on the epoxy acrylates may further comprise, for example, additives which are customary in the coatings industry, in the amounts customary for those additives: they include light stabilizers, curing accelerators, dyes, pigments, e.g. titanium dioxide pigment, devolatilizers, or else additional levelling agents.

Substrates suitable for coating include all surfaces amenable to cooling by actinic radiation. Examples include metals, plastics, wood, ceramic, stone, textile, leather, glass, including glass fibers, glass wool and rock wool, mineral-bound and resin-bound building materials, such as plasterboard panels, cement slabs or roof tiles. Accordingly the coating composition of the invention is suitable for applications such as automotive finishing, and also in particular for the coating of furniture and for Industrial coating, including coil coating and container coating. With the coating composition of the invention it is also possible in particular to coat primed or unprimed plastics such as, for example, ABS, AMMA, ASA, CA, CAB, EP, UF, CF, MP, MPF, PF, PAN, PA, PE, HDPE, LDPE, LLDPE, UHMWPE, PET, PMMA, PP, PS, SB, PUR, PVC, RF, SAN, PBT, PPE, POM, PUR-RIM, SMC, BMC, PP-EPDM and UP (abbreviations according to DIN 7728T1).

Unless indicated otherwise, parts and percentages in the examples and in the remainder of the description are by weight As common In the chemistry of epoxy compounds and especially for compounds produced on an industrial scale, the structural formulae are idealized and represent the largely predominant structure present.

EXAMPLES

Example 1

Preparation of

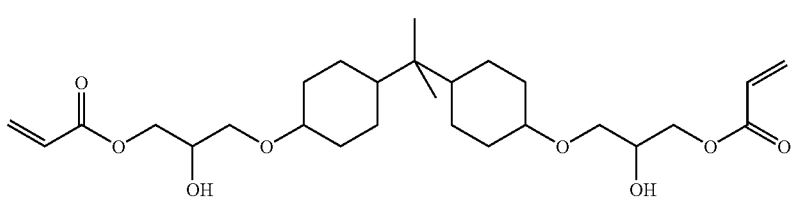

C

A mixture of 300 g of hydrogenated bisphenol A diglycidyl ether (1.275 eq of epoxide) and 0.39 g of di-tert-butyl-para-cresol (DBPC) is heated to 95° C., stirred and saturated with air using a gas introduction frit. Added dropwise to this mixture over the course of 22 minutes is a solution of 0.775 g of Cr$^{III}$ isooctanoate (Hexcem) in 22 ml of acrylic acid. The remaining 64 ml of acrylic acid (in all 87.3 g, 95 eq %) are metered in over 40 minutes. After a further five hours of stirring at 100° C. the mixture Is cooled to room temperature. The homogeneous, transparent, slightly greenish liquid has a viscosity of 48 Pa*s (25° C.), an epoxide content of 0.45 eq/kg and an acid content of 0.07 eq/kg.

Compounds A, B and E are prepared In precise analogy. The details of the compounds are summarized In Table 1.

Example 2

Preparation of a Mixture of Compounds A, D and E

A mixture of 150 g of tricyclodecanedimethanol diglycidyl ether (0.824 eq of epoxide), 100 g of triglycidyl isocyanurate (0.962 eq of epoxide), 50 g of DY-E (0.159 eq of epoxide) and 0.44 g of di-tert-butyl-para-cresol (DBPC) is heated to 95° C., stirred and saturated with air using a gas Introduction fit. Added dropwise to this mixture over the course of 14 minutes is a solution of 0.880 g of Cr$^{III}$ isooctanoate (Hexcem) in 24 ml of acrylic add. The remaining 94 ml of acrylic acid (in all 140.2 g, 95 eq %) are metered In over the course of 66 minutes. After a further five hours of stirring at 100° C. the mixture Is cooled to room temperature. The homogeneous, transparent, slightly greenish liquid has a viscosity of 34 Pas (25° C.), an epoxide content of 0.30 eq/kg and an acid content of 0.1 eq/kg.

TABLE 1

| | Compound | | | | |
|---|---|---|---|---|---|
| | A | B | C | A + D + E | E |
| Glycidyl ether | Tricyclodecane-dimethanol DGE[1] | Hydrogenated BPF-DGE[2] | Hydrogenated BPA-DGE[3] | Tricyclodecane-dimethanol DGE + TGIC + DY-E | DY-E[4] |
| Method | Example 1 | Example 1 | Example 1 | Example 2 | Example 1 |
| Appearance of epoxy acrylate | homogeneous, transparent, slightly greenish liquid | homogeneous, transparent, slightly greenish liquid | homogeneous, transparent, slightly greenish liquid | homogeneous, transparent, slightly greenish liquid | homogeneous, transparent, slightly greenish liquid |
| Viscosity[5] | 17 Pa*s (25° C.) | 22.4 Pa*s (25° C.) | 48 Pa*s (25° C.) | 34 Pa*s (25° C.) | 34 mPa*s (25° C.) |
| EP content[6] | 0.13 eq/kg | 0.273 eq/kg | 0.45 eq/kg | 0.3 eq/kg | 0.445 eq/kg |
| COOH content[7] | 0.02 eq/kg | 0.12 eq/kg | 0.07 eq/kg | 0.1 eq/kg | 0.14 eq/kg |

[1] prepared by reacting tricyclodecanedimethanol with epichlorohydrin
[2] prepared by reacting bisphenol F diglycidyl ether (Araldit ® GY285 Vantico) with $H_2$
[3] prepared by reacting bisphenol A diglycidyl ether (Araldit ® GY240 Vantico) with $H_2$
[4] monoglycidyl ether of the alcohol mixture $nC_{12}OH + nC_{13}OH + nC_{14}OH$
[5] cone and plate Brookfield viscometer, measurements with cone 06, 50 rpm at 25.0° C.
[6] tetraethylammonium bromide/HOAc, then 0.1N $HClO_4$ titration
[7] 0.1N KOH titration Examples 3–5

The table below symbolizes the investigations and the coatings obtained on the epoxy acrylates of the invention.

TABLE 2

| | Example | | | | |
|---|---|---|---|---|---|
| | 3 | 4 | 5 | Comp. 1 | Comp. 2 |
| Epoxy acrylate | A | B | A + D + E* | LR8713** | LR8765*** |
| Odour | none | none | none | solvent BuOAc | strong |
| Dose required to attain acetone resistance[1] | 41 | 65 | 26 | 104 | 26 |
| Persoz hardness [2] | 323 | 296 | 298 | 175 | 56 |
| Erichsen indentation [3] | 3.4 | 2.9 | 0.6 | 1.8 | 3.8 |
| Gloss retention Yellowing | 1000[4a] none[4a] | 1200[4a] none[4a] | n.d. none[4a] | 200[4b] about 150[4b] | Film detached within 100 h[4b] |
| Dose needed to attain scratch resistance[5] | 115 | 191 | 96 | 96 | 96 |

*in accordance with Example 2
**aromatic epoxy acrylate (BASF)
***aliphatic epoxy acrylate (BASF)
n.d.: not determined

[1] ... copper-laminated circuit board coated with undiluted resin containing 4% Irgacure ® 500 (Ciba Spezialitätenchemie) in 100 μm film thickness. Covered over with quartz glass web (11 discrete transmissions) and exposed using undoped high-pressure mercury vapour lamp with a UV dose of 1132 mJ/cm². Developed in acetone for 3 minutes and last undetached layer converted to dose. Result reported in mJ/cm².

[2] ... Persoz glass plate coated with undiluted resin containing 4% Irgacure ® 500 (Ciba Spezialitätenchemie) in 100 μm film thickness. Exposed using undoped high-pressure mercury vapour lamp with UV dose of 5560 mJ/cm². Persoz pendulum hardness determined in accordance with DIN EN ISO 1522 (average from two or more measurements). Result reported in seconds.

[3] ... Bonder 26 0 60C zinc-phosphatized steel plate coated with undiluted resin containing 4% Irgacure ® 500 (Ciba Spezialitätenchemie) in 50 μm film thickness. Exposed using undoped high-pressure mercury vapour lamp with UV dose of 5560 mJ/cm². Erichsen indentation determined in accordance with DIN EN ISO 1520 (average from two or more measurements). Result reported in mm.

[4a];[4b] ... Untreated aluminium plates coated with white-pigmented resin containing 1% Irgacure ® 819 (Ciba Spezialitätenchemie) in 50 μm film thickness. Exposed using gallium-doped high-pressure mercury vapour lamp with a UV dose of 1132 mJ/cm².
[4a] ... In WOM (Weather-O-matic) unit under standard conditions. Result reported in hours.
[4b] ... In QUV units, irradiated with UV. Result reported in hours.

[5] ... Black-painted card coated with undiluted resin containing 4% Irgacure 500 ® (Ciba Specialties) in 50 μm film thickness. Belt speed during irradiation with undoped high-pressure mercury vapour lamp increased until slight scratching with fingernail leaves a track. Result reported in mJ/cm² (belt speed).

Gloss Determination:

The gloss is determined in accordance with ISO 2813 standard.

The invention claimed is:

1. An epoxy acrylate selected from the group consisting of formula (A)

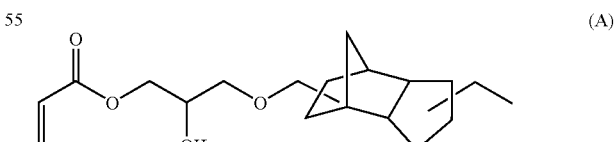

and formula (B)

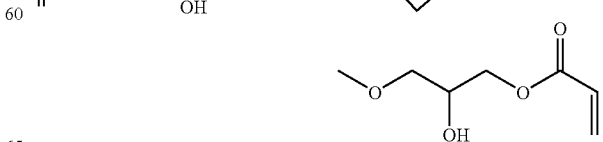

-continued

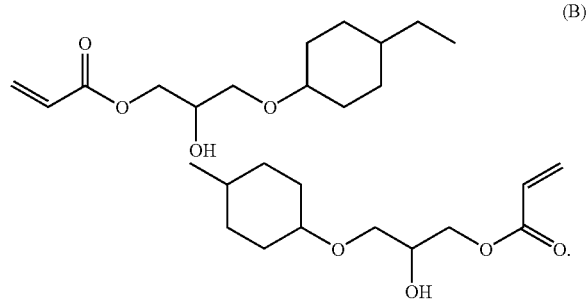

(B)

2. An epoxy acrylate mixture comprising at least two different epoxy acrylates selected from the group consisting of formula (A)

with the proviso that at least one epoxy acrylate is the epoxy acrylate of formula A or formula B.

3. The epoxy acrylate mixture according to claim 2 comprising at least 30% by weight of the epoxy acrylate of formula A and/or formula B.

4. The epoxy acrylate mixture according to claim 2 comprising at least 50% by weight of the epoxy acrylate of formula A and/or formula B.

5. A radiation-curable composition comprising an epoxy acrylate binder containing 5 to 90% by weight based on the total amount of binder of an epoxy acrylate selected from the group consisting of formula (A)

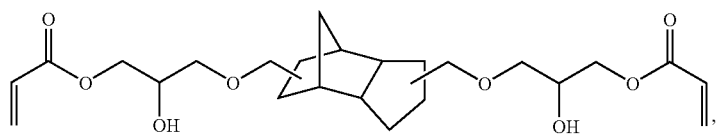

(A)

formula (B)

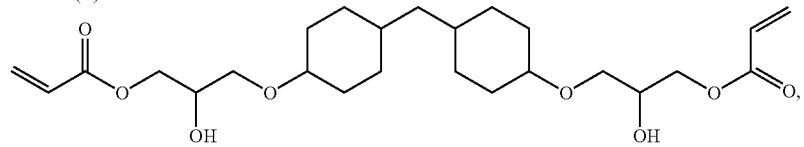

(B)

formula (C)

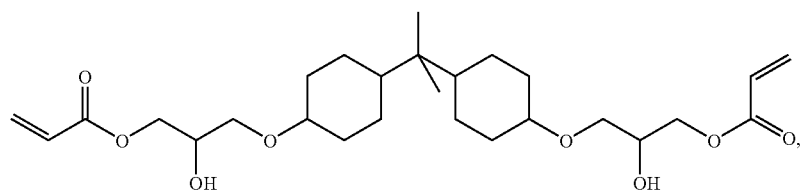

(C)

formula (D)

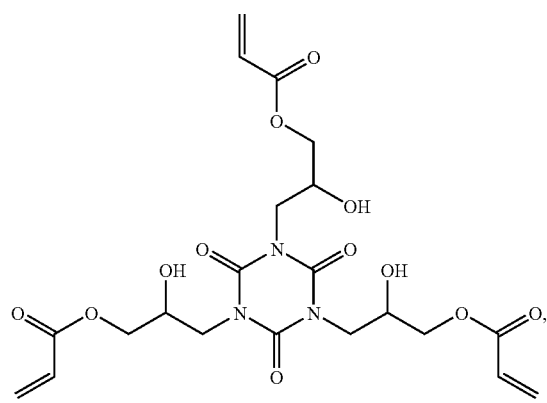

(D)

and formula (E)

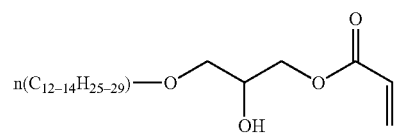

(E)

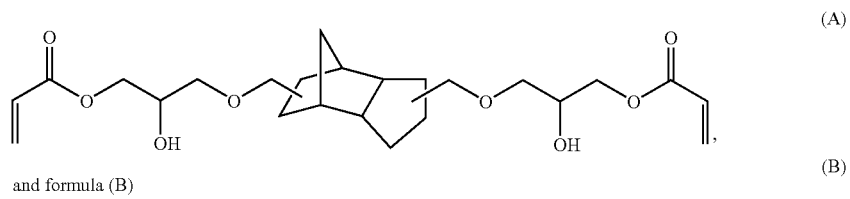
(A)
and formula (B)
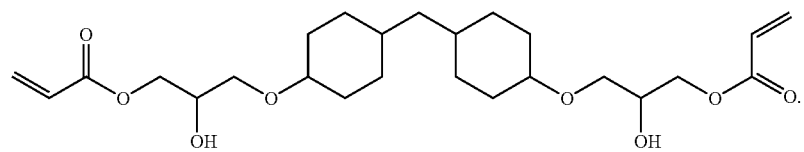
(B)
6. A radiation-curable composition comprising an epoxy acrylate binder containing 5 to 90% by weight based on the total amount of binder of an epoxy acrylate mixture comprising at least two different epoxy acrylates selected from the group consisting of formula (A)
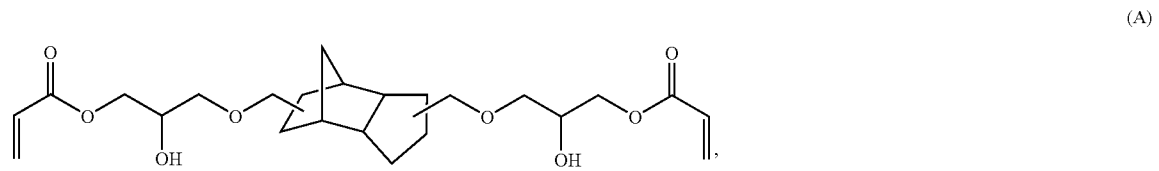
(A)
formula (B)
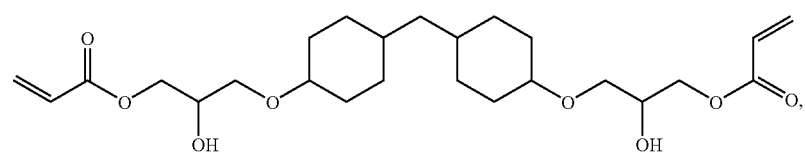
(B)
formula (C)
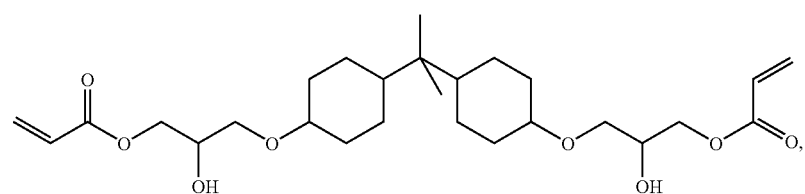
(C)
formula (D)
(D) and formula (E)
(E)
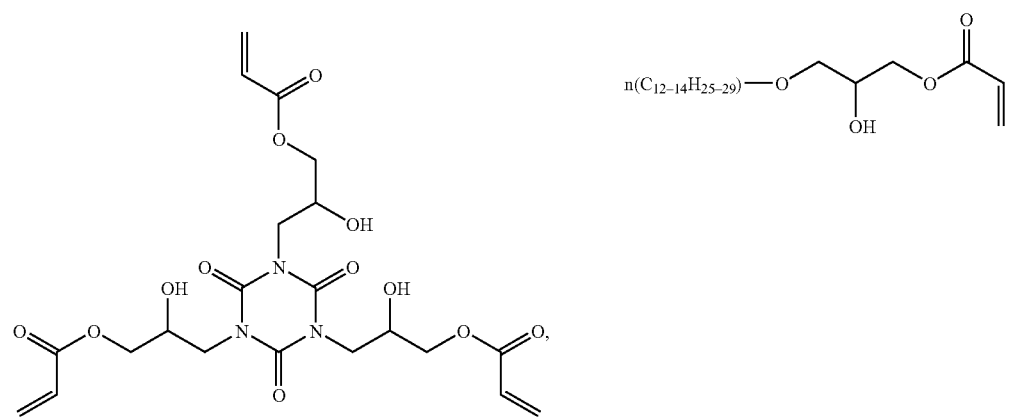

with the proviso that at least one of the epoxy acrylates is the epoxy acrylate of formula A or formula B.

7. A method for coating a substrate by applying the radiation-curable composition according to claim 5 to one or more surfaces of the substrate and curing the composition with radiation.

8. A method for coating a substrate by applying the radiation-curable composition according to claim 6 to one or more surfaces of the substrate and curing the composition with radiation.

9. A method for preparing an epoxy acrylate according to claim 1 by reacting acrylic acid with corresponding diglycidyl ether in a near-equinormal ratio of from 1:0.9 to 1:1.1.

10. A method for preparing an epoxy acrylate mixture according to claim 2 by reacting acrylic acid with corresponding diglycidyl ether in a near-equinormal ratio of from 1:0.9 to 1:1.1.

* * * * *